United States Patent [19]

Brattsand et al.

[11] Patent Number: 4,820,700
[45] Date of Patent: Apr. 11, 1989

[54] NOVEL ANDROSTANE-17β-CARBOXYLIC ACID ESTERS, A PROCESS AND INTERMEDIATES FOR THEIR PREPARATION, COMPOSITIONS AND METHOD FOR THE TREATMENT OF INFLAMMATORY CONDITIONS

[75] Inventors: Ralph L. Brattsand, Lund; Bror A. Thalen, Bjärred, both of Sweden

[73] Assignee: Aktiebolaget Draco, Lund, Sweden

[21] Appl. No.: 946,658

[22] Filed: Jan. 5, 1987

Related U.S. Application Data

[63] Continuation of Ser. No. 670,885, Nov. 13, 1984, abandoned.

[30] Foreign Application Priority Data

Nov. 18, 1983 [SE] Sweden ................. 8306370

[51] Int. Cl.$^4$ ................. A61K 31/58; C07J 71/00
[52] U.S. Cl. ................. 514/174; 540/70
[58] Field of Search ................. 514/174; 540/70

[56] References Cited

U.S. PATENT DOCUMENTS

| | | | |
|---|---|---|---|
| 4,119,625 | 10/1978 | Schmidlin | 260/397.1 |
| 4,198,336 | 4/1980 | Alvarez | 260/239.55 D |
| 4,198,403 | 4/1980 | Alvarez | 260/239.55 D |

FOREIGN PATENT DOCUMENTS

| | | | |
|---|---|---|---|
| 396079 | 9/1979 | Sweden | 260/239.55 D |
| 629824 | 5/1982 | Switzerland | 260/239.55 D |
| 634583 | 2/1983 | Switzerland | 260/239.55 D |

OTHER PUBLICATIONS

R. Brattsand, A. Thalen, K. Roempke, L. Kallstrom, E. Gruvstad—Influence of 16α,17α-Acetal Substitution and Steroid Nucleus Fluorination on the Topical to Systemic Activity Ratio of Glucocorticoids-1982.

R. Brattsand, A. Thalen, K. Roempke, L. Kallstrom, E. Gruvstad—Development of New Glucocorticosteroids with a Very High Ratio Between Topical; and Systemic Activities-1982.

Primary Examiner—Leonard Schenkman
Assistant Examiner—Joseph A. Lipovsky
Attorney, Agent, or Firm—Brumbaugh, Graves, Donohue & Raymond

[57] ABSTRACT

The invention refers to compounds having anti-inflammatory activity, characterized by the formula

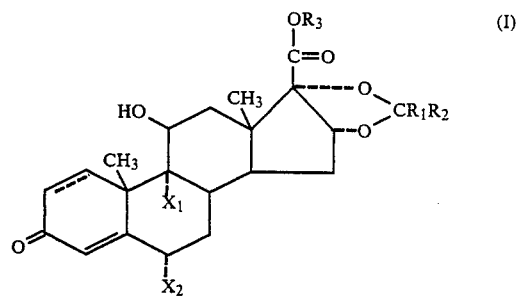

in the form of a stereoisomeric mixture or an epimer of the R or S type regarding the orientation of the substituents in the carbon atom at position 20, in which formula the 1,2 position is saturated or is a double bond, $X_1$ is hydrogen, fluorine, chlorine or bromine,
$X_2$ is hydrogen, fluorine, chlorine or bromine,
$R_1$ is hydrogen or methyl,
$R_2$ is a straight or branched hydrocarbon chain having 1-10 carbon atoms and
$R_3$ is hydrogen or a straight or branched chain alkyl group having 1-12 carbon atoms, a lower alkyl group substituted by 1-5 halogen atoms or an unsubstituted or substituted phenyl or benzyl group, provided that when $R_1$ is methyl $R_2$ is a hydrocarbon chain having 2-10 carbon atoms.

The invention also refers to a process and intermediates for the preparation of these compounds, a pharmaceutical preparation containing one of the compounds and a method for the treatment of inflammatory conditions.

10 Claims, No Drawings

NOVEL ANDROSTANE-17β-CARBOXYLIC ACID ESTERS, A PROCESS AND INTERMEDIATES FOR THEIR PREPARATION, COMPOSITIONS AND METHOD FOR THE TREATMENT OF INFLAMMATORY CONDITIONS

This application is a continuation of application Ser. No. 670,885, filed on 11/13/84 now abandoned.

DESCRIPTION

Technical Field

The present invention relates to novel, pharmacologically active compounds and a process and intermediates for their preparation. The invention also relates to pharmaceutical compositions containing the compounds and to methods of treatment of inflammatory conditions with these compounds.

The object of the invention is to provide a glucocorticosteroid which possesses a combination of high anti-inflammatory potency on the place of application and low glucocorticoid systemic potency.

BACKGROUND ART

It is known that certain glucocorticoids (GCS) can be used for local therapy of inflammatory, allergic or immunologic diseases in respiratory airways (e.g. asthma, rhinitis), in skin (eczema, psoriasis) or in bowel (ulcerative colitis, Morbus Crohn). With such local glucocorticoid therapy, clinical advantages over general therapy (with e.g. glucocorticoid tablets) are obtained, especially regarding reduction of the unwanted glucocorticoid effects outside the diseased area. To reach such clinical advantages, in e.g. severe respiratory airway disease, GCS must have a suitable pharmacological profile. They should have a combination of high intrinsic glucocorticoid activity at the application site but also a rapid inactivation by biotransformation (e.g. in the liver) after uptake into the general circulation. In laboratory models, the intrinsic glucocorticoid activity can be measured as local anti-inflammatory potency on the rat ear and the unwanted systemic glucocorticoid activity determined from the extent of thymus involution.

DISCLOSURE OF THE INVENTION

The present invention is based on the observation that certain 3-oxoandrost-4-ene- and 3-oxoandrosta-1,4-diene-17β-carboxylic acid esters possess anti-inflammatory potency on the place of application in combination with very low glucocorticoid systemic effects. The compounds of the invention can be used for the treatment and control of inflammatory conditions.

The compounds of the invention are characterized by the formula

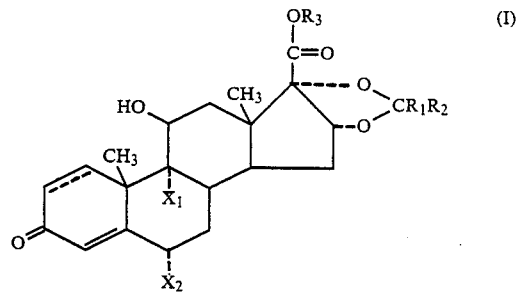

(I)

wherein
the 1,2-position is saturated or is a double bond $X_1$ is selected from hydrogen, fluorine, chlorine and bromine $X_2$ is selected from hydrogen, fluorine, chlorine and bromine $R_1$ is selected from hydrogen or methyl $R_2$ is selected from straight and branched hydrocarbon chains having 1-10 carbon atoms and $R_3$ represents hydrogen or a straight chain or branched alkyl group having 1-12 carbon atoms, a lower alkyl group (1-5 carbon atoms) substituted by 1-5 halogen atoms or an unsubstituted or substituted phenyl or benzyl group, provided that when $R_1$ is methyl $R_2$ is a hydrocarbon chain having 2-10 carbon atoms.

Halogen is chlorine, fluorine or bromine.

Substituted phenyl or benzyl means a phenyl or benzyl group substituted in the ortho-, meta- or para-position with a group —COO—alkyl(1-5C)

or

—CO—alkyl(1-5C)

The individual stereoisomeric components present in a mixture of a steroid having the above formula (I) can be elucidated in the following way:

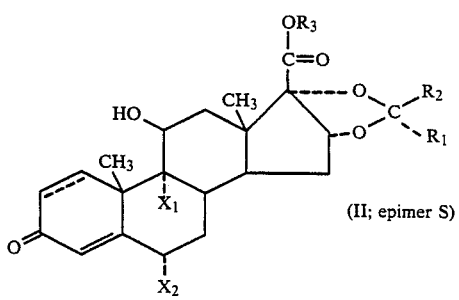

(II; epimer S)

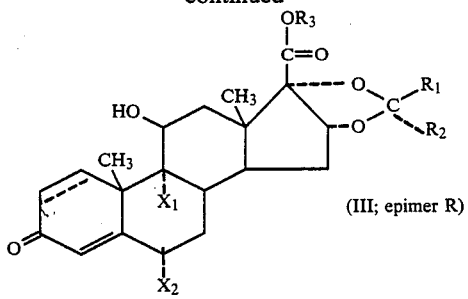

(III; epimer R)

In diastereoisomers like II and III, the configuration differs only at one (C-20) out of several asymmetric carbon atoms. Such diastereoisomers are denoted epimers.

The compounds of the invention are prepared by the oxidation of a compound of structure IV, V and VI to the corresponding 17β-carboxylic acid:

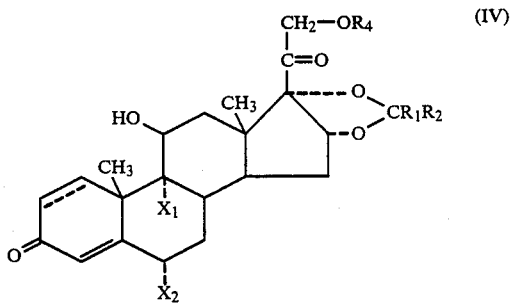

(IV)

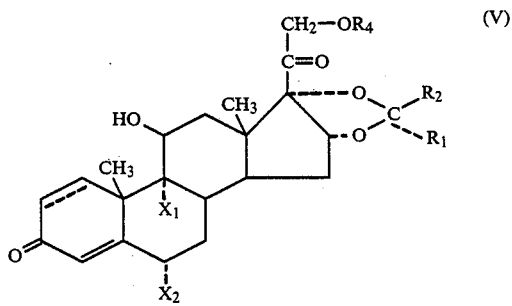

(V)

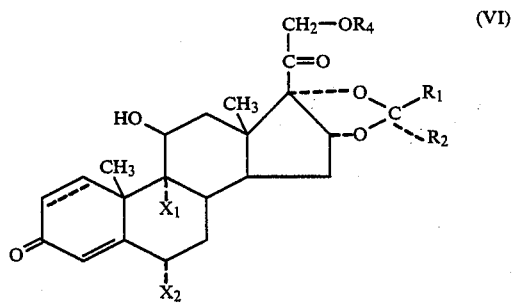

(VI)

wherein the solid and broken lines between C-1 and C-2 represent a single or double bond, $X_1$, $X_2$, $R_1$ and $R_2$ have the meaning given above, and $R_4$ is hydrogen or —OC—alkyl, wherein the alkyl moiety has 1-5 carbon atoms.

The 17β-carboxylic acids then are esterified to give compounds characterized by the formula I, II and III, wherein ⚌, $X_1$, $X_2$, $R_1$, $R_2$ and $R_3$ have the meaning given above.

The process of this invention to convert a compound of formulas IV, V or VI to the corresponding 17β-carboxylic acids is carried out in a suitable oxygenated hydrocarbon solvent such as a lower alkanol. Methanol and ethanol are preferred, particularly the former. The reaction medium is made slightly alkaline by the addition of a suitable weak inorganic base such as an alkali metal carbonate, for example sodium, lithium or potassium carbonate. The latter is preferred. The conversion of a compound of formula IV, V or VI to a 17β-carboxylic acid of formula I, II or III takes place at ambient temperatures, i.e. 20°–25° C.

The presence of oxygen is necessary for the reaction. Oxygen can be supplied by bubbling a stream of air or oxygen into the reaction mixture.

The oxidative degradation of the 17β side-chain of compounds of formula IV, V and VI to the corresponding 17β-carboxylic acids can also be carried out with periodic acid or with sodium bismuthate. The reaction is performed in a mixture of water and a suitable oxygenated hydrocarbon solvent such as a lower ether. Dioxane and tetrahydrofurane are preferred, particularly the former.

The parent 17β-carboxylic acids of compounds of formula I, II and III may be esterified in known manner to provide 17β-carboxylate esters according to the invention. For example, in order to prepare a lower alkyl ester, the 17β-carboxylic acid may be reacted with an appropriate diazoalkane, e.g. diazomethane, the reaction being preferably performed in a solvent medium, e.g. ether, tetrahydrofurane or methanol, and at a low temperature preferably at −5° C. to +30° C. Alternatively, the 17β-carboxylic acid may be reacted with an appropriate alcohol and a carbodiimide, e.g. dicyclohexylcarbodiimide, in a suitable solvent such as diethylether, tetrahydrofurane, methylene chloride or pyridine advantageously at a temperature of 25°–100° C. Alternatively, a salt of the 17β-carboxylic acid with an alkali metal, e.g. lithium, sodium or potassium, a salt of a quaternary ammonium compound, e.g. tetrabutylammonium, may be reacted with an appropriate alkylating agent, for example an alkyl halide or dialkylsulfate, e.g. dimethylsulfate, preferably in a polar solvent medium such as acetone, methylethylketone or dimethylformamide, conveniently at a temperature in the range 25°–100° C.

The crude steroid ester derivatives formed are after isolation purified by chromatography on a suitable material, for instance cross-linked dextran gels of Sephadex ® LH-type with suitable solvents as eluants, e.g. halogenated hydrocarbons, ethers, esters such as ethyl acetate or acetonitrile.

The individual 20R and 20S epimers, which are formed at the esterification with the epimeric mixtures of the acids, possess practically identical solubility characteristics. Accordingly, they have turned out to be impossible to separate and isolate from the epimeric mixture by conventional method for resolution of stereoisomers, e.g. fractionated crystallization. The process according to the invention consists in subjecting stereoisomeric mixtures according to the formula (I) above to column chromatography, the epimers 20R and 20S being separated in view of different mobility on the stationary phase, why they can be separately recovered. The chromatography may be carried out for instance on alkylsilanes or cyanoalkylsilanes of the type μBondapak $C_{18}$ and μBondapak CN in combination with a suitable mixture of organic solvents or a mixture of organic solvents and water as eluting agent. μBondapak $C_{18}$ is a octadecylsilane bonded phase and μBondapak CN is a cyanopropylsilane bonded phase prepared by Waters Associates, USA. As mobile phase a mixture of ethanol or methanol and water in the proportions 30–70:70:30 or heptane and ethanol in the proportions 80–100:0–20, respectively has successfully been used.

The compounds of the invention may be used for different modes of local administration dependent on the site of inflammation, e.g. percutaneously, parenterally or for local administration in the respiratory tract by inhalation. An important aim of the formulation design is to reach optimal bioavailability of the active steroid ingredient. For percutaneous formulations this is advantageously achieved if the steroid is dissolved with a high thermodynamic activity in the vehicle. This is attained by using a suitable system of solvents comprising suitable glycols, such as propylene glycols, such as propylene glycol or 1,3-butanediol either as such or in combination with water. It is also possible to dissolve the steroid either completely or partially in a lipophilic phase with the aid of a surfactant as a solubilizer. The percutaneous compositions can be an ointment, an oil in water cream, a water in oil cream or a lotion. In the emulsion vehicles the system comprising the dissolved active component can make up the disperse phase as well as the continuous one. The steroid can also exist in the above compositions as a micronized, solid substance.

Aerosols for steroids are intended for oral or nasal inhalation. The aerosol system is designed in such a way that each delivered dose contains 10–1000 μg, preferably 20–250 μg of the active steroid. The most active steroids are administered in the lower part of the dosage range. The micronized steroid consists of particles substantially smaller than 5 μm. In the pressurized aerosol the substance is suspended in a propellent gas mixture with the assistance of a dispersant, such as sorbitan trioleate, oleic acid, lecithin or sodium salt of dioctylsulphosuccinic acid.

WORKING EXAMPLES

The invention will be further illustrated by the following non-limitative examples. In the examples a flow-rate of 2.5 ml/cm$^2$.h$^{-1}$ is used at the preparative chromatographic runs. Molecular weights are in all examples determined with electron impact mass spectrometry and the melting points on a Leitz Wetzlar hot stage microscope. All HPLC analyses (HPLC=High Performance Liquid Chromatography) were, if not otherwise stated, performed on a Waters μBondapak $C_{18}$ column (300× 3.9 mm internal diameter) with a flow-rate of 1.0 ml/min and with ethanol-water in ratios between 50:50 and 60:40 as mobile phase, if not otherwise stated.

EXAMPLE 1

This example sets forth a process for preparing (20RS)-, (20R)- and (20S)-11β-hydroxy-16α,17α-alkylmethylenedioxyandrosta-1,4-diene-3-one-17β-carboxylic and -androst-4-ene-3-one-17β-carboxylic acids.

Preparation of (20RS)-11β-hydroxy-16α,17α-propylmethylenedioxyandrosta-1,4-diene-3-one-17β-carboxylic acid.

A. To a solution of 1.00 g of (22RS)-11β,21-dihydroxy-16α,17α-propylmethylenedioxypregna-1,4-diene-3,20-dione in 195 ml of ethanol 90 ml of 1% aqueous potassium carbonate was added. A stream of air was bubbled through this solution for about 20 h under stirring at room temperature. The ethanol was evaporated and 100 ml of water was added to the residue. This mixture was acidified with concentrated hydrochloric acid to pH 2 and extracted with ethyl acetate. The extracts were washed with 10% aqueous potassium carbonate. The aqueous phase was acidified with concentrated hydrochloric acid and extracted with ethyl acetate. After drying the solvent was evaporated and 3 ml of acetone was added to the residue. The precipitate formed was collected by filtration and dried to yield 742 mg of (20RS)-11β-hydroxy-16α,17α-propylmethylenedioxyandrosta-1,4-diene-3-one-17β-carboxylic acid, melting point 126°–30° C., molecular weight 416. Purity: 97.3% (HPLC: 0.01M acetic acid, 44:56); epimer 20R:20S, 85:15.

B. Periodic acid (575 mg) in 2 ml of water was added to a solution of (22RS)-11β,21-dihydroxy-16α,17α-propylmethylenedioxypregna-1,4-diene-3,20-dione in 7 ml of dioxane. The reaction mixture was stirred at room temperature for 4.5 h, neutralized with saturated aqueous sodium hydrogen carbonate and evaporated. The residue was dissolved in 60 ml of methylene chloride and washed with 6×25 ml 10% aqueous potassium carbonate. The aqueous phase was acidified with conc. hydrochloric acid and extracted with 4×50 ml of ethyl acetate. After drying the solvent was evaporated. The residue was dissolved in a small amount of ethyl acetate and precipitated with petroleum ether yielding 720 mg of (20RS)-11β-hydroxy-16α,17α-propylmethylenedioxyandrosta-1,4-diene-3-one-17β-carboxylic acid. The purity determined by HPLC was 97.8% and the ratio epimer 20R:20S was 45:55.

C. Preparation of (20R)-11β-hydroxy-16α,17α-propylmethylenedioxyandrosta-1,4-diene-3-one-17β-carboxylic acid.

To a solution of 1.00 g of (22R)-21-acetoxy-11β-hydroxy-16α,17α-propylmethylenedioxypregna-1,4-diene-3,20-dione in 150 ml of ethanol 150 ml of 10% aqueous potassium carbonate was added. A stream of air was bubbled through the solution for about 20 h under stirring at room temperature. The reaction mixture was worked up as in procedure A and precipitated from ethyl acetate-petroleum ether yielding 707 mg of (20R)-11β-hydroxy-16α,17α-propylmethylenedioxyandrosta-1,4-diene-3-one-17β-carboxylic acid.

D. Preparation of (20S)-11β-hydroxy-16α,17α-propyl-methylenedioxyandrosta-1,4-diene-3-one-17β-carboxylic acid.

To a solution of 1.00 g of (22S)-21-acetoxy-11β-hydroxy-16α,17α-propylmethylenedioxypregna-1,4-diene-3,20-dione in 150 ml of ethanol 150 ml of 10% aqueous potassium carbonate was added. A stream of air was bubbled through the solution for about 40 h under stirring at room temperature. The reaction mixture was worked up as in procedure A and precipitated from ethyl acetate-petroleum ether yielding 617 mg of (20S)-11β-hydroxy-16α,17α-propylmethylenedioxyandrosta-1,4-diene-3-one-17β-carboxylic acid.

E. Similarly, by following the procedure set forth in the example by substituting the 16α,17α-acetal between 16α-hydroxyprednisolone, triamcinolone and fluocinolone and acetaldehyde, propanal, butanal, isobutanal, pentanal, 3-methylbutanal, 2,2-dimethylpropanal, hexanal, heptanal, octanal, nonanal and dodecanal and their 21-esters (20RS)- (20R)- and (20S)-11β-hydroxy-16α,17α-alkylmethylenedioxyandrosta-1,4-diene- and 4-ene-3-one-17β-carboxylic acids and prepared (see Table 1 below).

TABLE 2

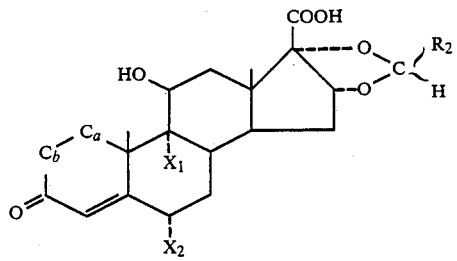

| $C_a-C_b$ | $X_1$ | $X_2$ | $R_2$ | Epimer | Yield (%) | Mp. * (°C.) | Molecular weight * calculated | found |
|---|---|---|---|---|---|---|---|---|
| —CH=CH— | H | H | CH$_3$ | 20R + S | 96 | | 388.5 | |
| —CH$_2$—CH$_2$— | H | H | (CH$_2$)$_2$CH$_3$ | 20R + S | 78 | | 418.5 | |
| —CH$_2$—CH$_2$— | H | H | (CH$_2$)$_2$CH$_3$ | 20R | 62 | | 418.5 | |
| —CH=CH— | F | H | (CH$_2$)$_2$CH$_3$ | 20S | 76 | 199–224 | 434.5 | 434 |
| —CH=CH— | F | H | (CH$_2$)$_2$CH$_3$ | 20R | 80 | 220–41 | 434.5 | 434 |
| —CH=CH— | F | F | (CH$_2$)$_2$CH$_3$ | 20R | 89 | | 452.5 | |
| —CH=CH— | H | H | (CH$_2$)$_4$CH$_3$ | 20S | 85 | | 444.6 | |
| —CH=CH— | H | H | (CH$_2$)$_4$CH$_3$ | 20R | 98 | | 444.6 | |

* Where no data is given the compounds have been used as intermediates for the preparation of the corresponding esters without further analysis.

EXAMPLE 2

Methyl(20RS)-11β-hydroxy-16α,17α-propylmethylenedioxyandrosta-1,4-diene-3-one-17β-carboxylate.

(20RS)-11β-hydroxy-16α,17α-propylmethylenedioxyandrosta-1,4-diene-3-one-17β-carboxylic acid (500 mg) and 611 mg of tetrabutylammonium hydrogen sulphate were added to 3 ml of 1M sodium hydroxide. A solution of 1 ml of methyl iodide in 20 ml of methylene chloride was added.

The mixture was refluxed with stirring for 1 h. The two layers were separated. The methylene chloride solution was dried and evaporated to a volume of 5 ml and 25 ml of ether was added to precipitate the tetrabutylammonium iodide which was removed by filtration. The solvents were evaporated and the residue purified by chromatography on a Sephadex® LH-20 column (72×6.3 cm) using chloroform as eluant. The fraction 1320–1545 ml was collected and evaporated yielding 289 mg of methyl(20RS)-11β-hydroxy-16α,17α-propylmethylenedioxyandrosta-1,4-diene-3-one-17β-carboxylate. The purity determined by HPLC was 99.8% and the ratio epimer 20R:20S, 49.6:50.4 (μBondapak CN column, heptane:ethanol, 95:5). Melting point: 128°–91° C. $[α]_D^{25} = +80°$ C. (c=0.200; CH$_2$Cl$_2$). The molecular weight was 430.

(20RS)-11β-Hydroxy-16α,17α-propylmethylenedioxyandrosta-1,4-diene-3-one-17β-carboxylic acid (100 mg) and methanol (0.01 ml) were added to 5 ml of dry pyridine. p-Toluenesulphonic acid (2 mg) was added and the mixture stirred for 15 min. Dicyclohexylcarbodiimide (60 mg) was added and the mixture was stirred at room temperature for 24 h. Acetic acid (0.2 ml) was added and the reaction mixture was kept overnight at 4° C. The precipitate formed was removed by filtration. Methylene chloride (16 ml) and ice (8 g) was added to the filtrate and 5M hydrochloric acid was then added with stirring until pH 2.5 was reached. The organic layer was washed with water, saturated sodium hydrogen carbonate and water, dried and evaporated. The residue was purified by chromatography on a Sephadex® LH-20 column (72×6.3 cm) using chloroform as eluant. The fraction 1455–1620 ml was collected and evaporated. The residue was dissolved in methylene chloride. Precipitation with petroleum ether yielded 27 mg of methyl(20RS)-11β-hydroxy-16α,17α-propylmethylenedioxyandrosta-1,4-diene-3-one-17β-carboxylate. The purity determined by HPLC was 99.5%. The ratio epimer 20R:20S was 51.2:48.8 (determined by HPLC, μBondapak CN column, heptane:ethanol, 95:5).

(20RS)-11β-Hydroxy-16α,17α-propylmethylenedioxyandrosta-1,4-diene-3-one-17β-carboxylic acid (42 mg) and potassium hydrogen carbonate (10 mg) were dissolved in 10 ml of dimethyl formamide. A solution of 21 mg of methyl iodide in 5 ml of dimethyl formamide was added and the reaction mixture stirred at room temperature overnight. Water (50 ml) was added and the mixture was extracted with methylene chloride. The combined extracts were washed with 5% aqueous sodium hydrogen carbonate and water, dried and evaporated. A yield of 26 mg of methyl(20RS)-11β-hydroxy-16α,17α-propylmethylenedioxyandrosta-1,4-diene-3-one-17β-carboxylate was obtained. The purity determined by HPLC was 98.5%.

EXAMPLES 3–16

The substances given in Table 2 below were prepared, isolated and purified in a manner analogous to that described in Example 2.

TABLE 2

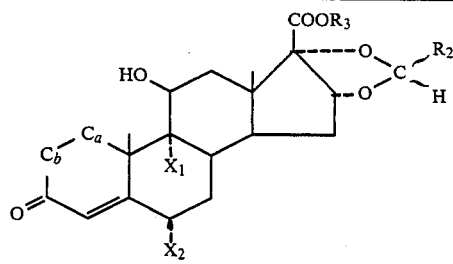

| Example No. | $C_a-C_b$ | $X_1$ | $X_2$ | $R_2$ | $R_3$ | Mp °C. | $[\alpha]_D^{25}$ (c = 0.2 in $CH_2Cl_2$) | Molecular weight calc. | found | Retention volume[1] (ml) |
|---|---|---|---|---|---|---|---|---|---|---|
| 3 | —CH=CH— | H | H | $CH_3$ | $CH_3$ | 212-41 | +89° | 402.5 | 402 | 1545-1815 |
| 4 | —$CH_2$—$CH_2$— | H | H | $(CH_2)_2CH_3$ | $CH_3$ | 110-47 | +115° | 432.6 | 432 | 1335-1530 |
| 5 | —CH=CH— | F | H | $(CH_2)_2CH_3$ | $CH_3$ | 204-10 | +77° | 448.5 | 448 | 1980-2235 |
| 6 | —CH=CH— | H | H | $(CH_2)_2CH_3$ | $CH_2CH_3$ | 163-74 | +77° | 444.6 | 444 | 1380-1620 |
| 7 | —CH=CH— | F | H | $(CH_2)_2CH_3$ | $CH_2CH_3$ | 210-42 | +74° | 462.6 | 462 | 1815-2115 |
| 8 | —CH=CH— | H | H | $(CH_2)_2CH_3$ | $(CH_2)_3CH_3$ | 147-59 | +83° | 472.6 | 472 | 1260-1485 |
| 9 | —CH=CH— | H | H | $(CH_2)_2CH_3$ | $C(CH_3)_3$ | 174-204 | | 472.6 | 472 | 1530-1770 |
| 10 | —CH=CH— | H | H | $(CH_2)_2CH_3$ | $CH_2Cl$ | 186-90 | +76° | 465.0 | 464 | 1575-1860 |
| 11 | —CH=CH— | H | H | $(CH_2)_2CH_3$ | $C_6H_5$ | 252-62 | +127° | 492.6 | 492 | 230-55[2] |
| 12 | —CH=CH— | H | H | $(CH_2)_2CH_3$ | $m\text{-}C_6H_5COOCH_3$ | 160-63 | +119° | 550.7 | 550 | 1335-1575 |
| 13 | —CH=CH— | H | H | $(CH_2)_2CH_3$ | $p\text{-}C_6H_5COOCH_3$ | 206-28 | +135° | 550.7 | 550 | 1275-1650 |
| 14 | —CH=CH— | H | H | $(CH_2)_2CH_3$ | $p\text{-}C_6H_5COCH_3$ | 191-221 | +138° | 534.7 | 534 | 1320-1635 |
| 15 | —CH=CH— | H | H | $(CH_2)_2CH_3$ | $CH_2C_6H_5$ | 186-91 | +87° | 506.6 | 506 | 2010-2385[3] |
| 16 | —CH=CH— | H | H | $(CH_2)_4CH_3$ | $CH_3$ | 162-77 | +73° | 458.6 | 458 | 1425-1680 |

[1] On a Sephadex LH-20 column (72 × 6.3 cm) using chloroform as eluant
[2] On a Sephadex LH-20 column (83 × 2.5 cm) using chloroform as eluant
[3] On a Sephadex LH-20 column (76 × 6.3 cm) using heptane:chloroform:ethanol, 20:20:1, as eluant.

EXAMPLE 17

Methyl(20R)-11β-hydroxy-16α,17α-propylmethylenedioxyandrosta-1,4-diene-3one-17β-carboxylate.

(20R)-11β-Hydroxy-16α,17α-propylmethylenedioxyandrosta-1,4-diene-3-one-17β-carboxylic acid (500 mg) and 611 mg of tetrabutylammonium hydrogen sulphate were added to 3 ml of 1M sodium hydroxide. A solution of 1 ml of methyl iodide in 20 ml of methylene chloride was added. The mixture was refluxed with stirring for 1 h. The two layers were separated. The methylene chloride solution was dried and the volume reduced to 5 ml. Ether (25 ml) was added to precipitate the tetrabutylammonium iodide, which was removed by filtration. The solvents were evaporated and the residue purified by chromatography on a Sephadex ® LH-20 column (72×6.3 cm) using chloroform as eluant. The fraction 1395-1665 ml was collected and evaporated yielding 295 mg of methyl(20R)-11β-hydroxy-16α,17α-propylmethylenedioxyandrosta-1,4-diene-3-one-17β-carboxylate. The purity determined by HPLC was 99.1%. Melting point: 210°-14° C. $[\alpha]_D^{25} = +82°$ C. (c=0.266; $CH_2Cl_2$). The molecular weight was 430.

EXAMPLE 18

Methyl(20S)-11β-hydroxy-16α,17α-propylmethylenedioxyandrosta-1,4-diene-3-one-17β-carboxylate.

(20S)-11β-Hydroxy-16α,17α-propylmethylenedioxyandrosta-1,4-diene-3-one-17β-carboxylic acid (617 mg) and 754 mg tetrabutylammonium hydrogen sulphate were added to 3.7 ml of 1M sodium hydroxide. A solution of 1M of methyl iodide in 20 ml of methylene chloride was added. The reaction mixture was refluxed with stirring for 1 h and isolated as in Example 11. The crude product was purified by chromatography on a Sephadex ® LH-20 column (72×6.3 cm) using chloroform as eluant. The fraction 1440-1725 ml was collected and evaporated yielding 377 mg of methyl(20S)-11β-hydroxy-16α,17α-propylmethylenedioxyandrosta-1,4-diene-3-one-17β-carboxylate. The purity determined by HPLC was 99.3%. Melting point: 175°-84° C. $[\alpha]_D^{25} = +72°$ C. (c=0.232; $CH_2Cl_2$). The molecular weight was 430.

EXAMPLES 19-24

The substances given in Table 3 below were prepared, isolated and purified in a manner analogous to that described in Examples 17 and 18.

TABLE

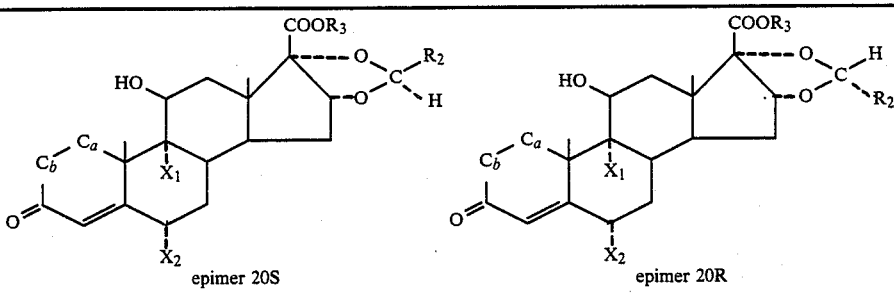

epimer 20S        epimer 20R

| Example No. | $C_a$-$C_b$ | $X_1$ | $X_2$ | $R_2$ | $R_3$ | Epimer | Mp °C. | $[\alpha]_D^{25}$ (c = 0.2 in $CH_2Cl_2$) | Molecular weight calc. | found | Retention volume[1] (ml) |
|---|---|---|---|---|---|---|---|---|---|---|---|
| 19 | —$CH_2$—$CH_2$— | H | H | $(CH_2)_2CH_3$ | $CH_3$ | 20R | 166–74 | +128° | 432.6 | 432 | 1350–1560 |
| 20 | —CH=CH— | F | H | $(CH_2)_2CH_3$ | $CH_3$ | 20S | 260–63 | +69° | 448.5 | 448 | 1920–2220 |
| 21 | —CH=CH— | F | H | $(CH_2)_2CH_3$ | $CH_3$ | 20R | 209–10 | +78° | 448.5 | 448 | 1980–2160 |
| 22 | —CH=CH— | F | F | $(CH_2)_2CH_3$ | $CH_3$ | 20R | 223–26 | | 466.5 | 466 | 430–95[2] |
| 23 | —CH=CH— | H | H | $(CH_2)_4CH_3$ | $CH_3$ | 20S | 197–203 | +67° | 458.6 | 458 | 1425–1680 |
| 24 | —CH=CH— | H | H | $(CH_2)_4CH_3$ | $CH_3$ | 20R | 190–93 | +79° | 458.6 | 458 | 1425–1635 |

[1]On a Sephadex LH-20 column (72 × 6.3 cm) using chloroform as eluant.
[2]On a Saphadex LH-20 column (83 × 2.5 cm) using chloroform as eluant.

EXAMPLE 25. PHARMACEUTICAL PREPARATIONS

The following non-limitative examples illustrate formulations intended for different topical forms of administration. The amount of active steroid in the percutaneous formulations are ordinarily 0.001–0.2% (w/w), preferably 0.01–0.1% (w/w).

| Formulation 1, Ointment | |
|---|---|
| Steroid, micronized | 0.025 g |
| Liquid paraffin | 10.0 g |
| White soft paraffin | ad 100.0 g |
| Formulation 2, Ointment | |
| Steroid | 0.025 g |
| Propylene glycol | 5.0 g |
| Sorbitan sesquioleate | 5.0 g |
| Liquid paraffin | 10.0 g |
| White soft paraffin | ad 100.0 g |
| Formulation 3, Oil in water cream | |
| Steroid | 0.025 g |
| Cetanol | 5.0 g |
| Glyceryl monostearate | 5.0 g |
| Liquid paraffin | 10.0 g |
| Cetomacrogol 1000 | 2.0 g |
| Citric acid | 0.1 g |
| Sodium citrate | 0.2 g |
| Propylene glycol | 35.0 g |
| Water | ad 100.0 g |
| Formulation 4, Oil in water cream | |
| Steroid, micronized | 0.025 g |
| White soft paraffin | 15.0 g |
| Liquid paraffin | 5.0 g |
| Cetanol | 5.0 g |
| Sorbimacrogol stearate | 2.0 g |
| Sorbitan monostearate | 0.5 g |
| Sorbic acid | 0.2 g |
| Citric acid | 0.1 g |
| Sodium citrate | 0.2 g |
| Water | ad 100.0 g |
| Formulation 5, Water in oil cream | |
| Steroid | 0.025 g |
| White soft paraffin | 35.0 g |
| Liquid paraffin | 5.0 g |
| Sorbitan sesquioleate | 5.0 g |
| Sorbic acid | 0.2 g |
| Citric acid | 0.1 g |
| Sodium citrate | 0.2 g |
| Water | ad 100.0 g |
| Formulation 6, Lotion | |
| Steroid | 0.25 mg |
| Isopropanol | 0.5 ml |
| Carboxyvinylpolymer | 3 mg |
| NaOH | q.s. |
| Water | ad 1.0 g |
| Formulation 7, Suspension for injection | |
| Steroid, micronized | 0.05–10 mg |
| Sodium carboxymethylcellulose | 7 mg |
| NaCl | 7 mg |
| Polyoxyethylene (20) sorbitan monooleate | 0.5 mg |
| Phenyl carbinol | 8 mg |
| Water, sterile | ad 1.0 ml |
| Formulation 8, Pressurized aerosol for oral and nasal inhalation | |
| Steroid, micronized | 0.1% w/w |
| Sorbitan trioleate | 0.7% w/w |
| Trichlorofluoromethane | 24.8% w/w |
| Dichlorotetrafluoromethane | 24.8% w/w |
| Dichlorodifluoromethane | 49.6% w/w |
| Formulation 9, Solution for atomization | |
| Steroid | 7.0 mg |
| Propylene glycol | 5.0 g |
| Water | ad 10.0 g |
| Formulation 10, Powder for inhalation A gelatin capsule is filled with a mixture of | |
| Steroid, micronized | 0.1 mg |
| Lactose | 20 mg |

The powder is inhaled by means of an inhalation device.

PHARMACOLOGICAL TESTS

All steroids according to the present invention are physiologically active compounds. The glucocorticoid properties of the compounds have been compared with those of budesonide ([22R,S]-16α,17α-butylidenedioxy-11β,21-dihydroxypregna-1,4-diene-3,20-dione) as this compound is one of the glucocorticoids which has reached most far towards the desired combination of high local but low systemic effects (results with this reference in rats—R. Brattsand et al.: Europ. J. Respir. Dis. 63 suppl. 122, 62, 1982; in man—S. Å. Johansson et al.: Europ. J. Respir. Dis. 63 suppl. 122, 74, 1982).

The local anti-inflammatory activity of the compounds has been investigated as the potency to prevent ear edema according to the following procedure. Ear edemas were induced on male rats, weighing about 90 g, by application of 20 μl/side of ear of 5% ethyl phenylpropiolate (Aldrich Co.) dissolved in acetone. Two hours later the ear edema was measured with a special micrometer (Oditest, H. C. Kröplin, Gmbh, Messzeug Fabrik). The glucocorticoids were applied as pretreatment 16 hours before induction of the edemas by application of 20 μl/side of ear in solutions of acetone (0.08–250 μg steroid/ml=0.0064–20 μg/rat). Six ears were tested per dose. The relative potency of the test compounds to prevent ear edemas was calculated with linear regression analysis in relation to the reference compound budesonide.

For the new compounds the doses used in the ear edema test do not induce systemic glucocorticoid actions. To be able to judge the systemic potency of the new compounds, they were administered in higher doses by the oral or intratracheal routes according to the following procedure. The sex and age of the rats were the same as described above. The glucocorticoids were suspended in a vehicle of CMC-Na 0.75 g, Tween 80 0.04 g and NaCl 0.7% w/w ad 100 g. On oral administration the suspension was given by gavage in a volume of 0.5 ml. On intratracheal deposition the rats were lightly anaesthetized and were hanging on a slanted board and 0.1 ml was instilled in the trachea via the oropharynx. At least 5 doses were tested per compound within the range 40–10240 (oral) or 20–5120 μg/rat (intratracheal route). Each dose group comprised 4 rats. The animals were killed after 4 days and the thymus weight recorded. The relative potency of the compounds was calculated by linear regression analysis in relation to the reference substance budesonide.

The results of the testing of glucocorticoids of the invention in accordance with the procedure given above are shown in Table 4. The table shows that the new compounds have surprisingly low systemic glucocorticoid activity of the same low magnitude as for hydrocortisone, while most new compounds have a much higher local anti-inflammatory potency than this reference. The compounds in example 2, 5, 7, 17, 18, 21 and 22 reach a much higher ratio between local and systemic glucocorticoid activities than what is recorded for budesonide and for hydrocortisone.

To effectively and safely treat inflammatory and allergic diseases of e.g. the airways or skin in large patient groups, there is a demand for compounds which possess sufficient local activity and an improved ratio between this local activity and the untoward systemic effects. The new compounds of this invention comply with these two claims at the same time.

TABLE 4

Local and systemic glucocorticoid effects of tested compounds

| Example no. | Epimer | Local anti-inflammatory potency (LAIP) | Systemic glucocorticoid potency after oral adm. (SPO) | Systemic glucocorticoid potency after intratracheal adm. (SPI) | Therapeutic ratio between local systemic potencies LAIP/SPO | LAIP/SPI |
|---|---|---|---|---|---|---|
| 2 | 20R + S | 0.20 | 0.02 | 0.02 | 10 | 10 |
| 3 | 20R + S | 0.07 | — | — | — | — |
| 4 | 20R + S | 0.07 | — | — | — | — |
| 5 | 20R + S | 0.30 | 0.04 | — | 7.5 | — |
| 6 | 20R + S | 0.05 | — | — | — | — |
| 7 | 20R + S | 0.03 | <0.01 | — | >3 | — |
| 10 | 20R + S | 0.11 | — | — | — | — |
| 16 | 20R + S | 0.10 | — | — | — | — |
| 17 | 20R | 0.30 | 0.03 | 0.02 | 10 | 15 |
| 18 | 20S | 0.03 | <0.01 | <0.01 | >3 | >3 |
| 20 | 20S | 0.03 | — | — | — | — |
| 21 | 20R | 0.60 | 0.01 | — | >10 | — |
| 22 | 20R | 2.00 | <0.10 | — | ≧20 | — |
| Budesonide | 22R + S | 1 | 1 | 1 | 1 | 1 |
| Hydrocortisone | — | 0.0002 | 0.02 | — | <1 | — |

BEST MODE OF CARRYING OUT THE INVENTION

Among the compounds of the present invention those described in example 2 (methyl(20RS)-11β-hydroxy-16α,17α-propylmethylenedioxyandrosta-1,4-diene-3-one-17β-carboxylate), ex. 17 (methyl(20R)-11β-hydroxy-16α,17α-propylmethylenedioxyandrosta-1,4-diene-3-one-17β-carboxylate), ex. 5 (methyl(20RS)-9α-fluoro-11β-hydroxy-16α,17α-propylmethylenedioxyandrosta-1,4-diene-3-one-17β-carboxylate), ex. 21 (methyl(20R)-9α-fluoro-11β-hydroxy-16α,17α-propylmethylenedioxyandrosta-1,4-diene-3-one-17β-carboxylate) and ex. 22 (methyl(20R)-6α,9α-difluoro-11β-hydroxy-16α,17α-propylmethylenedioxyandrosta-1,4-diene-3-one-17β-carboxylate) are the preferred ones.

The 20R-epimer is the preferred epimer.

We claim:

1. A compound of the formula

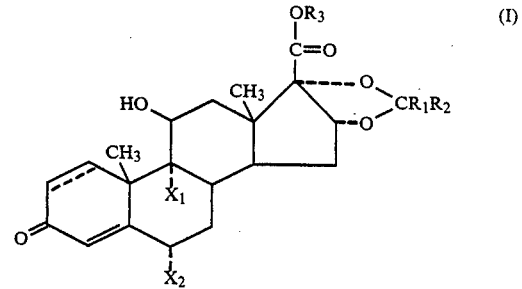

(I)

in the form of a stereoisomeric mixture or an epimer of the R or S type regarding the orientation of a substituents in the carbon atom at position 20, in which formula the 1,2-position is saturated or is double bond, $X_1$ is hydrogen, fluorine, chlorine or bromine, $X_2$ is hydrogen, fluorine, chlorine or bromine, $R_1$ is hydrogen or methyl, $R_2$ is n-propyl, and R₃ is hydrogen or a straight or branched chain alkyl group having 1-12 carbon atoms, a lower alkyl group substituted by 1-5 halogen atoms or an unsubstituted or substituted phenyl or benzyl group.

2. A compound according to claim 1 in the form of the 20R-epimer.

3. An anti-inflammatory pharmaceutical preparation comprising an effective amount of a compound according to any of claims 1-2 together with a pharmaceutically acceptable carrier.

4. A pharmaceutical preparation according to claim 3 in dosage unit form.

5. A method for the treatment and control of inflammatory conditions in mammals, including man, comprising administering to a host in need of such treatment of an effective amount of a compound according to any of claims 1-2.

6. An intermediate characterized by the formulas

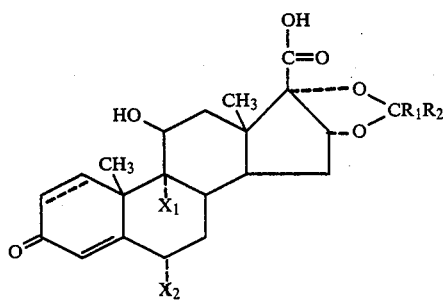

or

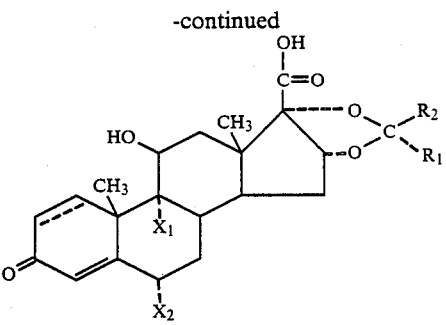

or

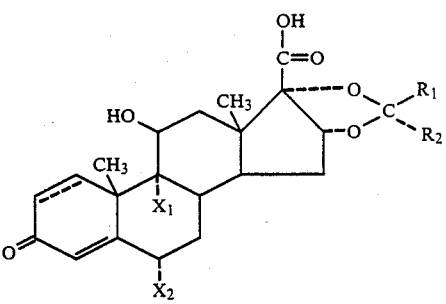

wherein the dashed line between the C-1 and C-2 positions represents single or double bond,
$X_1$ is hydrogen, fluorine, chlorine or bromine,
$X_2$ is hydrogen, fluorine, chlorine or bromine,
$R_1$ is hydrogen or methyl,
$R_2$ is N-propyl.

7. An intermediate according to claim 6, wherein $R_1$ is hydrogen.

8. A compound according to claim 1, wherein $R_1$ is hydrogen.

9. A pharmaceutical preparation comprising a compound according to claim 8 together with a pharmaceutically acceptable carrier.

10. A method for the treatment and control of inflammatory conditions in mammals, including man, comprising administering to a host in need of such treatment an effective amount of a compound according to claim 8.

* * * * *

UNITED STATES PATENT AND TRADEMARK OFFICE
CERTIFICATE OF CORRECTION

PATENT NO. : 4,820,700

DATED : April 11, 1989

INVENTOR(S) : Ralph L. Brattsand; Bror A. Thalen

It is certified that error appears in the above-identified patent and that said Letters Patent is hereby corrected as shown below:

col. 6, lines 65-66, "-16α, 1-7α-" should read ---16α, 17α---;

col. 7, line 1, "TABLE 2" should read --TABLE 1--;

cols. 11 & 12, line 1, "TABLE" should read --TABLE 3--;

col. 11, line 60, Table 3, "Water ad 100.09" should read --Water ad 100.0g--;

col. 14, line 7, Table 4, 2 right table cols. "local systemic" should read --local and systemic--;

col. 13, Table 4, Example no. 7, "20R°S" should read --20R+S--;

col. 14, lines 35-36, "-16α, 1-7α-" should read ---16α, 17α---;

col. 14, lines 39-40, "-16α, 1-7α-" should read ---16α, 17α---;

Signed and Sealed this

Second Day of June, 1992

*Attest:*

DOUGLAS B. COMER

*Attesting Officer*   *Acting Commissioner of Patents and Trademarks*